(12) United States Patent
Kobayashi et al.

(10) Patent No.: US 9,040,300 B2
(45) Date of Patent: May 26, 2015

(54) METHOD OF WASHING ADHERENT CELL USING TREHALOSE-CONTAINING CELL-WASHING SOLUTION

(71) Applicant: OTSUKA PHARMACEUTICAL FACTORY, INC., Tokushima (JP)

(72) Inventors: Eiji Kobayashi, Tokushima (JP); Tamaki Wada, Tokushima (JP); Masako Doi, Tokushima (JP)

(73) Assignee: OTSUKA PHARMACEUTICAL FACTORY, INC., Tokushima (JP)

( * ) Notice: Subject to any disclaimer, the term of this patent is extended or adjusted under 35 U.S.C. 154(b) by 0 days.

(21) Appl. No.: 14/035,100

(22) Filed: Sep. 24, 2013

(65) Prior Publication Data
US 2014/0093961 A1  Apr. 3, 2014

(30) Foreign Application Priority Data

Sep. 28, 2012 (JP) ................................. 2012-216630

(51) Int. Cl.
*C12N 5/0775* (2010.01)
*A61K 35/28* (2006.01)

(52) U.S. Cl.
CPC .............. *A61K 35/28* (2013.01); *C12N 5/0663* (2013.01); *C12N 2500/34* (2013.01); *C12N 2501/734* (2013.01)

(58) Field of Classification Search
None
See application file for complete search history.

(56) References Cited

U.S. PATENT DOCUMENTS

| 5,486,359 | A | 1/1996 | Caplan et al. | |
|---|---|---|---|---|
| 2002/0076445 | A1* | 6/2002 | Crowe et al. | 424/532 |
| 2013/0260461 | A1* | 10/2013 | Kobayashi et al. | 435/375 |

FOREIGN PATENT DOCUMENTS

| EP | 0 580 444 A1 | 7/1993 |
|---|---|---|
| EP | 0 580 444 A1 | 1/1994 |
| EP | 2 639 296 A1 | 9/2013 |
| JP | 3253131 B2 | 2/2002 |
| WO | 2007/043698 A1 | 4/2007 |
| WO | 2012/063870 A1 | 5/2012 |
| WO | 2012/133575 A1 | 10/2012 |

OTHER PUBLICATIONS

Di G. et al. Development and Evaluation of a Trehalose Contained Solution Formula to Preserve hUC-MSCs at 4 Degrees C. J of Cellular Physiology 227(3)879-884, Mar. 2012.*
Chem, F., Yonsei Med. J. vol. 45, 2004, pp. 1107-1114.
Batle, E. et al., Cell vol. 111, 2002, pp. 251-263.
Morrison, S.J. et al., Cell vol. 96, 1999, pp. 737-749.
Gage, F.H., Science vol. 287, 2000, pp. 1433-1438.
First Examination Report issued with respect to NZ No. 615872, mail date is Oct. 1, 2013.
Extended European Search Report issued with respect to European Patent Application No. 13185828A, mail date is Dec. 20, 2013.
E.C. López-Díez et al., "The Interaction of trypsin with trehalose: an investigation of protein preservation mechanisms", Biochimica et Biophysica Acta (2004) pp. 139-148.
Lia H. Campbell et al., "Culturing with trehalose produces viable endothelial cells after cryopreservation", Cryobiology 64 (2012) pp. 240-244.
Hirofumi Noguchi et al., "Comparison of M-Kyoto Solution and Histidine-Tryptophan-Ketoglutarate Solution With a Trypsin Inhibitor for Pancreas Preservation in Islet Transplantation", pp. 655-658, Sep. 2007, 84 (5).

* cited by examiner

*Primary Examiner* — Ralph Gitomer
(74) *Attorney, Agent, or Firm* — Greenblum & Bernstein, P.L.C.

(57) ABSTRACT

Methods of washing adherent cells, capable of effectively suppressing cell death due to proteolytic enzyme treatment for detaching the adherent cell from a culture vessel and subsequent cell treatment; cell-washing solutions used for the washing method; methods of producing cell suspensions for transplantation using the cell-washing solution; and kits comprising the cell-washing solution. Trehalose or its derivative or a salt thereof is added to physiological aqueous solutions to prepare cell-washing solutions containing trehalose or its derivative or a salt thereof as an active ingredient. The cell-washing solutions can be used to wash adherent cells before detaching the adherent cells from a culture vessel by proteolytic enzyme treatment to suppress cell death due to the proteolytic enzyme treatment. The concentration of trehalose applied to the cell-washing solution may be a concentration capable of suppressing the cell death due to the proteolytic enzyme treatment, such as 0.1 to 20 (w/v) %.

7 Claims, 4 Drawing Sheets

Figure 4

METHOD OF WASHING ADHERENT CELL USING TREHALOSE-CONTAINING CELL-WASHING SOLUTION This application claims priority to Japanese application 2012-216630 filed Sep. 28, 2012.

TECHNICAL FIELD

The present invention relates to a method of washing an adherent cell, comprising washing the adherent cell using a cell-washing solution comprising a physiological aqueous solution added with trehalose or its derivative or a salt thereof before detaching the adherent cell from a culture vessel by proteolytic enzyme treatment; the cell-washing solution for use in the washing method; a method of producing a cell suspension for transplantation by using the cell-washing solution, a kit for producing a cell suspension for transplantation comprising the cell-washing solution; and the like.

RELATED ART

In recent years, rapid progress of stem cell studies has increased momentum toward regenerative medicine, and the knowledge and understanding thereof has been widespread not only in researchers but also in the public. Regenerative medicine using stem cells is medicine intended for reestablishing the function of cells and tissues damaged by various diseases by utilizing the self-renewal potential and multipotency of stem cells or factors secreted by stem cells. Bone-marrow transplantation in patients having intractable hematological diseases such as leukemia and aplastic anemia results in the engraftment of hematopoietic progenitors in the body of these patients, which enables the maintenance of hematopoietic capacity over almost entire life. Recently, many researchers have aimed at clinical application using stem cells other than hematopoietic stem cells, have identified stem cells in central nerves, peripheral nerves, bone marrow, small intestine, and the like, and have begun to implement the tissue stem cell transplantation treatment of traumatic disease and tissue degeneration disease (Non-patent Documents 1 to 3).

Stem cells used for transplantation treatment can be collected in an extremely low amount from the living body; thus, it has generally been carried out to proliferate the collected stem cells by in vitro subculture (Patent Document 1). A proteolytic enzyme, such as trypsin, may be used in detaching stem cells from a culture vessel during subculture; however, it is problematic if cells are damaged by proteolytic enzyme treatment and die at a certain rate. In order to implement regenerative medicine of high quality, although it is necessary to provide a sufficient amount (number) of stem cells, it is simultaneously important to provide high quality cells, namely, stem cells (population) in which the percentage of living cells is high; thus, there is an urgent need for the development of a method capable of suppressing cell death due to proteolytic enzyme treatment during subculture.

Trehalose is a type of disaccharide formed by the 1,1-glycoside linkage of glucoses. Trehalose is used in various foods and cosmetics because it has a sweet taste and a high water-retaining capacity. Trehalose is also used as an active ingredient of an organ-protecting solution in transplanting the organ because it has the properties of stabilizing cell membrane and suppressing cell damage. Excellent organ-protecting solutions containing trehalose have been developed, such as ET-Kyoto solution and New ET-Kyoto solution (Patent Documents 2 and 3 and Non-patent Document 4). However, it is unclear whether the washing of adherent cells with a trehalose-containing physiological aqueous solution before detaching the cells from a culture vessel by a proteolytic enzyme such as trypsin can suppress cell death due to the proteolytic enzyme treatment.

PATENT DOCUMENTS

Patent Document 1: U.S. Pat. No. 5,486,359
Patent Document 2: Japanese Patent No. 3253131
Patent Document 3: International Publication No. WO 2007/043698

NON-PATENT DOCUMENTS

Non-patent Document 1: Gage, F. H. Science 287: 1433-1438 (2000)
Non-patent Document 2: Morrison, S. J. et al., Cell 96: 737-749 (1999)
Non-patent Document 3: Batle, E. et al., Cell 111: 251-263 (2002)
Non-patent Document 4: Chem, F. et al., Yonsei Med. J. 45: 1107-1114 (2004)

SUMMARY OF THE INVENTION

Object to be Solved by the Invention

An object of the present invention is to provide a method of washing an adherent cell, capable of effectively suppressing cell death due to proteolytic enzyme treatment for detaching the adherent cell from a culture vessel and subsequent cell treatment; a cell-washing solution used for the washing method; a method of producing a cell suspension for transplantation using the cell-washing solution; and a kit comprising the cell-washing solution.

Means to Solve the Object

The present inventors found that the washing of mesenchymal stem cell detached from a cell culture vessel by proteolytic enzyme treatment with a trehalose-containing physiological aqueous solution suppressed the death of the mesenchymal stem cells (Japanese Patent Application No. 2011-072068). Because the damage of cells by proteolytic enzyme treatment induced a pathway of cell death (apoptosis or the like), such an effect by trehalose was considered to be due to the suppression of an apoptosis pathway or the promotion of the function repairing the cell damage. However, in intensive studies for solving the above problems, it has been found that when cells happened to be washed with a trehalose-containing lactated Ringer's solution (hereinafter abbreviated as "LRT") before proteolytic enzyme treatment, cell death could be effectively suppressed compared to the case of using lactated Ringer's solution (hereinafter abbreviated as "LR") or phosphate buffered saline (PBS) as a control or the case of washing cells with LRT after proteolytic enzyme treatment, thereby accomplishing the present invention.

Specifically, the present invention relates to (1) a method of washing an adherent cell, comprising washing the adherent cell using a cell-washing solution comprising a physiological aqueous solution with trehalose or its derivative or a salt thereof added, before detaching the adherent cell from a culture vessel by proteolytic enzyme treatment, (2) the method according to (1), wherein the adherent cell is a mesenchymal stem cell, and (3) the method according to (1) or (2), wherein the cell-washing solution comprises trehalose or its derivative or a salt thereof in a concentration of 1 to 15 (w/v) %.

The present invention also relates to (4) a cell-washing solution for washing an adherent cell before detaching the adherent cell from a culture vessel by proteolytic enzyme treatment, comprising a physiological aqueous solution added with trehalose or its derivative or a salt thereof, (5) the cell-washing solution according to (4), wherein the adherent cell is a mesenchymal stem cell, and (6) the cell-washing solution according to (4) or (5), comprising trehalose or its derivative or a salt thereof in a concentration of 1 to 15 (w/v) %.

The present invention also relates to (7) a method of producing a cell suspension for transplantation, comprising the steps of (a) removing a medium in a culture vessel to which an adherent cell is adhered and washing the adherent cell with a cell-washing solution comprising a physiological aqueous solution added with trehalose or its derivative or a salt thereof; (b) detaching the adherent cell from the culture vessel by proteolytic enzyme treatment; (c) suspending the adherent cell detached from the culture vessel in a protein-containing physiological aqueous solution to make a cell suspension; and (d) removing the solution in the cell suspension and washing the adherent cell with the physiological aqueous solution, (8) the production method according to (7), wherein the adherent cell is a mesenchymal stem cell, (9) the production method according to (7) or (8), wherein the cell-washing solution of the step (a) comprises trehalose or its derivative or a salt thereof in a concentration of 1 to 15 (w/v) %, (10) the production method according to any one of (7) to (9), wherein the proteolytic enzyme of the step (b) is trypsin, (11) the production method according to any one of (7) to (10), wherein the protein-containing physiological aqueous solution of the step (c) further comprises trehalose or its derivative or a salt thereof, (12) the production method according to any one of (7) to (11), wherein the protein-containing physiological aqueous solution of the step (c) is a serum-containing basal medium for animal cell culture, and (13) the production method according to any one of (7) to (12), wherein the physiological aqueous solution of the step (d) further comprises trehalose or its derivative or a salt thereof.

The present invention also relates to (14) a kit for producing a cell suspension for transplantation, comprising the cell-washing solution according to any one of (4) to (6), and a package insert describing an effect of suppressing cell death due to proteolytic enzyme treatment by the cell-washing solution.

The present invention also relates to (15) use of trehalose or its derivative or a salt thereof in the production of a cell-washing solution for washing an adherent cell before detaching the adherent cell from a culture vessel by proteolytic enzyme treatment.

The present invention further relates to (16) trehalose or its derivative or a salt thereof for use to wash an adherent cell before detaching the adherent cell from a culture vessel by proteolytic enzyme treatment.

Other embodiments of the present invention can include a combination of a physiological aqueous solution and trehalose or its derivative or a salt thereof for washing an adherent cell before detaching the adherent cell from a culture vessel by proteolytic enzyme treatment, and trehalose or its derivative or a salt thereof for use by adding to a physiological aqueous solution to wash an adherent cell before detaching the adherent cell from a culture vessel by proteolytic enzyme treatment. In addition, other embodiments of the present invention can include an in vitro subculture method for an adherent cell, comprising washing the adherent cell by using a physiological aqueous solution comprising trehalose or its derivative or a salt thereof, and a kit for in vitro subculture of an adherent cell, comprising trehalose or its derivative or a salt thereof and a package insert describing an effect of suppressing cell death due to proteolytic enzyme treatment.

Effect of the Invention

According to the present invention, the rate of dead cells can be decreased in a cell suspension for transplantation containing stem cells such as mesenchymal stem cells, and a good-quality cell suspension for transplantation in regenerative medicine can be provided.

MODE OF CARRYING OUT THE INVENTION

The washing method of the present invention is a method which involves, in particular embodiments, washing an adherent cell, such as a mammalian cell, in a culture vessel from which a medium is removed in advance with an aspirator or the like, using the cell-washing solution of the present invention containing a physiological aqueous solution and trehalose or its derivative or a salt thereof (hereinafter referred to as "a trehalose") added to the physiological aqueous solution, namely, a physiological aqueous solution containing trehalose, before detaching the adherent cell from the culture vessel by proteolytic enzyme treatment, where the cell-washing solution of the present invention is intended to be specific for use as a cell-washing solution for washing an adherent cell before detaching the adherent cell from a culture vessel by proteolytic enzyme treatment. For the purpose of the present invention, an adherent cell means an anchorage-dependent cell capable of survival, proliferation, and substance production by adhering to the anchorage. Specific examples of adherent cells can include, but are not limited to, multipotent stem cells (embryonic stem cells i.e., "ES" cells, EG cells, iPS cells, and the like), mesenchymal stem cells, neural stem cells, myeloid stem cells, and germ stem cells; among those, mesenchymal stem cells are preferable. Examples of mammals can include, but are not limited to, rodents, such as mice, rats, hamsters, and guinea pigs; lagomorphs, such as rabbits; ungulates such as pigs, cows, goats, horses, and sheep; carnivores, such as dogs and cats; and primates, such as humans, monkeys, rhesus monkey, cynomolgus monkey, marmosets, orangutans, and chimpanzees; among those, mice, pigs, and humans can be preferably exemplified. Examples of the mammalian cells can include, but are not limited to, mammalian pancreatic islet cells intravenously administered to patients with type I diabetes, and mammalian dendritic cells, natural killer cells, $\alpha\beta$ T cells, $\gamma\delta$ T cells, and cytotoxic T lymphocytes (CTL) intravenously administered to cancer patients, in addition to mammalian stem cells administered via the blood vessel for regenerative medicine or the like.

The physiological aqueous solution applied to the cell-washing solution of the present invention is not particularly limited, provided that it is an isotonic aqueous solution in which the concentrations of salt and sugar and the like are adjusted with sodium, potassium, and the like, so as to provide generally same osmotic pressure as that of body fluid or cell fluid. Specific examples thereof can include, but are not limited to, physiological saline, salines having a buffering effect (phosphate buffered saline or "PBS," and Tris buffered saline or "TBS," and HEPES buffered saline, and the like), Ringer's solutions (lactated Ringer's solution, acetated Ringer's solution, bicarbonated Ringer's solution, and the like), a 5% glucose aqueous solution, basal media for animal cell culture (DMEM, EMEM, RPMI-1640, $\alpha$-MEM, F-12, F-10, M-199, and the like), and isotonic agents (grape sugar, D-sorbitol, D-mannitol, lactose, sodium chloride, and the like); among those, preferred are salines having a buffering effect and Ringer's solutions, more preferably PBS and lactated Ringer's solution. The physiological aqueous solution may be one commercially available or of one's own preparation. Examples of the commercially available one can include, but are not limited to, D-PBS (−) (from Invitrogen), physiological saline ("Otsuka Normal Saline" from Otsuka Pharmaceutical Factory, Inc.), lactated Ringer's solution (Lactec Injection from Otsuka Pharmaceutical Factory, Inc.), and a medium kit specific for human mesenchymal stem cells (from Lonza Group Ltd.). As used herein, "isotonic" means that the osmotic pressure is in the range of 250 to 380 mOsm/l. The physiological aqueous solution may further contain, for example, a stabilizer (for example, human serum albumin or polyethylene glycol), a buffer (for example, phosphate buffer or sodium acetate buffer), a chelating agent (for example, EDTA, EGTA, citric acid, or salicylate), a solubilizer, a preservative, an antioxidant, etc.

Examples of trehalose as a trehalose as applied to the cell-washing solution of the present invention can include, but are not limited to, $\alpha,\beta$-trehalose as a disaccharide in which $\alpha$-glucose and $\beta$-glucose are 1,1-glycoside-linked, and $\beta,\beta$-trehalose as a disaccharide in which 2 $\beta$-glucose molecules are 1,1-glycoside-linked, in addition to $\alpha,\alpha$-trehalose as a disaccharide in which 2 $\alpha$-glucose molecules are 1,1-glycoside-linked; among those, $\alpha,\alpha$-trehalose is preferable. These trehaloses can be produced by any method, such as chemical synthesis, production by a microorganism, and production by an enzyme; however, commercially available ones can also be used. Examples thereof can include $\alpha,\alpha$-Trehalose (from Hayashibara Co., Ltd.) and $\alpha,\alpha$-Trehalose (from Wako Pure Chemical Industries, Ltd.).

The trehalose derivative as a trehalose as applied to the cell-washing solution of the present invention is not particularly limited, provided that it is a glycosyltrehalose in which one or more sugar units are bonded to trehalose as disaccharide; glycosyltrehaloses include glycosyltrehalose, maltosyltrehalose, and maltotriosyltrehalose.

Examples of salts of trehalose or its derivative as trehalose as applied to the cell-washing solution of the present invention can include, but are not limited to, acid addition salts such as hydrochlorides, hydrobromates, hydroiodides, phosphates, nitrates, sulfates, acetates, propionates, toluenesulfonates, succinates, oxalates, lactates, tartrates, glycolates, methanesulfonates, butyrates, valerates, citrates, fumarates, maleates, and malates; metal salts such as sodium salts, potassium salts, and calcium salts; and ammonium salts and alkylammonium salts. These salts are each used in the form of a solution at the time of use, and their action preferably has the same potency as that of trehalose. These salts may form hydrates or solvates, and may be used alone or in a proper combination of two or more thereof.

The concentration of a trehalose as applied to the cell-washing solution of the present invention may be a concentration capable of suppressing (inhibiting) cell death (apoptosis, necrosis, or the like) due to proteolytic enzyme treatment, and the optimal condition thereof can be properly selected depending on the type of the cell, the number of cells in a culture vessel, the concentration of cells, and the like. A higher concentration of a trehalose generally has a higher effect capable of suppressing the cell death due to proteolytic enzyme treatment; however, too high a concentration of the trehalose has the possibility of adversely affecting the survival of cells. For example, the concentration of trehalose as applied to the cell-washing solution of the present invention is typically 0.1 (w/v) % or more, preferably 1.0 (w/v) % or more, more preferably 3.0 (w/v) % or more, and is typically 20 (w/v) % or less, preferably 15 (w/v) % or less, more preferably 7.0 (w/v) % or less, still more preferably 5.0 (w/v) % or less in view of avoiding a deleterious effect on the rate of survival of cells. Thus, the concentration of trehalose in the cell-washing solution may be, for example, 0.1 to 20 (w/v) %, preferably 1.0 to 15 (w/v) %, more preferably 1.0 to 7.0 (w/v) %, still more preferably 3.0 to 5.0 (w/v) %. The ability of the cell-washing solution of the present invention to suppress cell death can be confirmed by using any method capable of detecting cell death, such as a trypan blue staining method, TUNEL method, Nexin method, or FLICA method.

Examples of the proteolytic enzyme used for the proteolytic enzyme treatment of the present invention can include, but are not limited to, trypsin, lysylendopeptidase, pronase, pepsin, elastase, and collagenase; among those, trypsin can be preferably shown as an example.

The conditions, such as temperature and time, during the washing of adherent cells, for the washing method of the present invention may be conditions under which the effect of trehalose of the present invention is observed and the cells are not damaged; the temperature is typically in the range of 20 to 37° C. and the treatment time is typically in the range of 1 second to 20 minutes. However, the effect of trehalose of the present invention may be observed to the same extent at least in the treatment time range of 30 seconds to 10 minutes; thus, the treatment time is preferably 30 seconds to 10 minutes. The number of washing operations may be at least once and may also be plural times (2, 3, 4 times, or more); however, once is preferable in view of time effectiveness and cost effectiveness.

The cell-washing solution of the present invention can be used to produce a cell suspension for transplantation as follows.

The above-described adherent cells are generally first subcultured in vitro in a culture vessel for adherent cells (a multiwell-plate, a culture dish, e.g., a petri dish or dish, a flask, or the like) coating-treated with cell adhesion molecules (fibronectin, vitronectin, laminin, nidogen, or the like) or a polymer (poly-L-ornithine, poly-lysine, or the like), or a surface-treated culture vessel for adherent cells. A factor inhibiting the activity of a proteolytic enzyme, such as a protease inhibitor, may be contained in the medium, or the function of the proteolytic enzyme may be competitively inhibited by an excessive amount of protein present in the medium. Thus, before performing proteolytic enzyme treatment in the next step, the medium in the culture vessel to which adherent cells adhere is removed with an aspirator or the like in advance, followed by washing the cells with the cell-washing solution of the present invention containing little or no protein to remove the remaining medium. Conditions such as temperature and time in the washing treatment can include the above conditions during the washing of adherent cells for the washing method of the present invention.

Then, the adherent cells are detached from the culture vessel by proteolytic enzyme treatment. On this occasion, the cells are typically damaged, decreasing the cell survival rate in the cell population; however, the effect of trehalose of the present invention can suppress (inhibit) the decrease in the cell survival rate.

The proteolytic enzyme treatment is generally performed by contacting the cells with an aqueous solution containing the proteolytic enzyme. The aqueous solution containing the proteolytic enzyme may be an aqueous solution in which a commercially available proteolytic enzyme powder from Gibco or the like is dissolved in the above physiological aqueous solution, or a commercially available proteolytic enzyme solution from Lonza Group Ltd. or the like, diluted with the physiological aqueous solution. The concentration of the proteolytic enzyme in the aqueous solution containing the proteolytic enzyme may be a concentration sufficient to detach the cells depending on the type of the proteolytic enzyme, and is typically in the range of 0.05 to 0.25 (w/v) %.

The conditions such as temperature and time for proteolytic enzyme treatment may be conditions under which most (70 to 100%) of the cells can be detached from the culture vessel; the temperature is typically in the range of 20 to 37° C., and the treatment time is typically in the range of 15 seconds to 15 minutes. The proteolytic enzyme treatment of cells over a sustained period of time may typically damage the cells, decreasing the survival rate thereof; however, the cells difficult to detach from a culture vessel in a typical treatment time can be treated for a long period of time (10 to 30 minutes or the like), to suppress the decrease in the cell survival rate.

Subsequently, to stop the proteolytic enzyme treatment, the adherent cells detached from the culture vessel are generally suspended in a protein-containing physiological aqueous solution. The suspension can be carried out by a method well-known in the art, such as pipetting or tapping. The protein-containing physiological aqueous solution may be a physiological aqueous solution containing a protein in an amount sufficient to suppress the activity of the proteolytic enzyme. Specific examples thereof can include, for example, the physiological aqueous solution described above, containing 0.1 to 30 (v/v) % serum (fetal bovine serum, i.e., "FBS," calf bovine serum, i.e., "CS," or the like); preferred is the basal medium for animal cell culture described above, containing FBS. The protein-containing physiological aqueous solution preferably further contains trehalose as described above because an additive or synergistic effect due to combination with trehalose of the present invention is observed.

Then, to remove the proteolytic enzyme in the cell suspension and wash the adherent cells, the solution in the cell suspension is removed, followed by washing the adherent cells by using the above-described physiological aqueous solution as a washing solution after the proteolytic enzyme treatment. The removal of the solution in the cell suspension can be carried out by separating the cell suspension into the supernatant (solution) and the precipitate (cells) using a centrifuge and removing the supernatant using an aspirator or the like. To enhance the washing effect, the precipitate is preferably suspended by pipetting, tapping, or the like. The number of washings of the cells in the cell suspension may be at least once, and may also be plural times (2, 3, 4 times, or more); however, it is preferably once in view of time effectiveness and cost effectiveness. The above-described physiological aqueous solution used as a washing solution after proteolytic enzyme treatment preferably further contains trehalose as described above because an additive or synergistic effect due to combination with the trehalose of the present invention is observed.

The cells after washing are generally separated into the supernatant (solution) and the precipitate (cells), for example, using a centrifuge, and, after removing the supernatant using an aspirator or the like, suspended in an aqueous solution for transplantation suitable for transplantation via means such as intra-arterial, intra-venous, or percutaneous means. Specific examples of the aqueous solution for transplantation can include the above-described physiological aqueous solutions; preferred is Ringer's solution, more preferably lactated Ringer's solution, acetated Ringer's solution, or bicarbonated Ringer's solution, still more preferably lactated Ringer's solution.

Examples of the in vitro subculture method for adherent cells according to another aspect can include a method sequentially comprising the steps of (a') removing the medium in the above-described culture vessel to which adherent cells adhere and washing the adherent cells with the cell-washing solution of the present invention; (b') detaching the adherent cells from the culture vessel by the proteolytic enzyme treatment using the above-described proteolytic enzyme; (c') suspending the detached adherent cells in the above-described protein-containing physiological aqueous solution; and (d') subculturing a portion (50 [v/v]%, 25 [v/v] %, 12 [v/v]%, or the like) of the cell suspension using a fresh culture vessel; more preferred is a method further comprising the step of (p) removing the solution in the cell suspension and washing the adherent cells with the above-described physiological aqueous solution or protein-containing physiological aqueous solution, between the steps (c') and (d').

The culture temperature applied to the subculture is typically in the range of about 30 to 40° C. and is preferably 37° C. The $CO_2$ concentration during culture is typically in the range of about 1 to 10% and is preferably about 5%. The humidity during culture is typically in the range of about 70 to 100% and is preferably about 95 to 100%.

Examples of the medium applied to the subculture can include the basal medium for animal cell culture described above, containing serum (FBS, CS, or the like) in the range of 0.1 to 30 (v/v) % and the basal medium for animal cell culture described above, containing additives necessary for cell proliferation in place of serum. Examples of the additives can include, for example, iron sources (transferrin and the like), growth factors (insulin, EGF, basic FGF, glial cell line-derived neurotrophic factor (GDNF), stem cell factors (SCF) and the like), polyamines (putrescine and the like), steroids (progesterone, β-estradiol, and the like), minerals (selenous acid or its salt), adhesion factors (for example, heparin, heparan sulfate, collagen, and fibronectin), and reducing agents (N-acetylcysteine, 2-mercaptoethanol, catalase, and the like). These media may also contain, for example, saccharides such as glucose, an antibiotic such as streptomycin, penicillin, or gentamicin, a buffer such as Hepes, in addition to a stem cell differentiation inhibitor (LIF, Wnt, TGF-β, and the like) necessary for maintaining the undifferentiated state of stem cells.

In the production method for a cell suspension for transplantation according to the present invention or the above in vitro subculture method for an adherent cell according to another aspect, each step is preferably aseptically carried out using a clean bench or the like in order to avoid the contamination of dust, bacteria, and the like.

The kit for producing a cell suspension for transplantation according to the present invention or the kit for in vitro subculture of an adherent cell according to another aspect is not particularly limited provided that it is limited to use as a kit for producing a cell suspension for transplantation or limited to use as a kit for in vitro subculture of an adherent cell, and comprises the cell-washing solution of the present invention and a package insert describing the effect of suppressing cell death due to proteolytic enzyme treatment. They may further comprise the above-described proteolytic enzyme and a pipette, a centrifuge tube, and the like, and can be particularly preferably exemplified by those further comprising the above-described proteolytic enzyme.

The present invention will be more specifically described below with reference to Examples. However, these Examples are not intended to limit the technical scope of the present invention.

EXAMPLES

Example 1

1. Confirmation of Suppression of Cell Death by Use of Cell-Washing Solution of Present Invention as Cell-Washing Solution before Proteolytic Enzyme Treatment 1-1 Material
1-1-1 3 (w/v) % Trehalose-Containing Lactated Ringer's Solution 3 g of trehalose (from Hayashibara Co., Ltd.) was mixed with 90 mL of lactated Ringer's solution ("Lactec Injection" from Otsuka Pharmaceutical Factory, Inc.), which was then dissolved using a stirrer. The resultant was adjusted to a volume of 100 mL with the lactated Ringer's solution and then sterilized using a 0.22-μm filter in a safety cabinet, and 10 mL each was dispensed.

1-1-2 Human Mesenchymal Stem Cells from Bone Marrow (hMSC-BM)

hMSC-BM (from Lonza Group Ltd.) was prepared according the procedures described in [1] to [9] below and used in the present experiment.

[1] hMSC-BM was cultured in a 5% $CO_2$ incubator at 37° C. in the presence of a medium kit specific for human mesenchymal stem cells (from Lonza Group Ltd.) (hereinafter referred to as "MSC medium") using a 75-$cm^2$ flask. The condition of the cells was observed under a microscope, and culture was performed until a confluent state of about 90% was reached.

[2] The MSC medium was removed using an aspirator, and the cells were rinsed with 8 mL/flask of Dulbecco's phosphate buffered saline (D-PBS [–]) (hereinafter simply referred to as "PBS") (from Invitrogen).

[3] PBS was removed using an aspirator, and 3.75 mL/flask of trypsin-EDTA (from Lonza Group Ltd.) was added, followed by standing at room temperature for 5 minutes.

[4] The flask was gently shaken while the cells were observed under a microscope until about 90% thereof were detached.

[5] 3.75 mL/flask of MSC medium was added to stop the trypsin reaction, and the cells were recovered by pipetting and transferred to a 50-mL centrifuge tube.

[6] Centrifugation was carried out at 600×g and 22° C. for 5 minutes.

[7] The MSC medium as the supernatant was removed using an aspirator, and 5 mL/flask of MSC medium was added, followed by suspending the cell pellet (precipitate).

[8] 10 μL of the cell suspension was taken and mixed with 10 μL of 0.4% trypan blue (from Gibco) to measure the number of live cells using a cell counter.

[9] The cells were seeded in a 6-well dish to $1×10^5$ cells/2 mL/well, and then cultured in a 5% $CO_2$ incubator at 37° C. The whole amount of the MSC medium was exchanged with a fresh medium every 3 to 4 days.

1-2 Method

To confirm that the use of the cell-washing solution of the present invention as a cell-washing solution before proteolytic enzyme treatment suppresses cell death, an experiment was carried out according to the procedures described in [1] to [5] below.

[1] The MSC medium was aspirated/removed from the 6-well dish to which hMSC-BM adhered, to which 2 mL/well of lactated Ringer's solution containing 3 (w/v) % trehalose (3% LRT) at 25° C. was then added, followed by incubation at 25° C. for 1 minute (washing treatment before enzyme treatment). PBS was used as a control.

[2] After aspirating/removing 3% LRT, 1 mL/well of trypsin-EDTA (from Lonza Group Ltd.) maintained at 25° C. was added, followed by incubation at 25° C. for 15 minutes (enzyme treatment).

[3] The MSC medium at 25° C. was added by 1 mL to suspend the cells (enzyme reaction termination treatment), and then the cell suspension was transferred to a 15-mL conical centrifuge tube.

[4] Centrifugation was carried out at 600×g and 25° C. for 5 minutes, and the supernatant was aspirated/removed, followed by suspension in 100 μL of ice-cold PBS for each well (washing treatment after enzyme treatment).

[5] 10 μL of the cell suspension was taken and mixed with 10 μL of trypan blue, followed by measuring the number of cells using one cell counter under a microscope to evaluate the rate of dead cells.

1-3 Result

Figure 1:
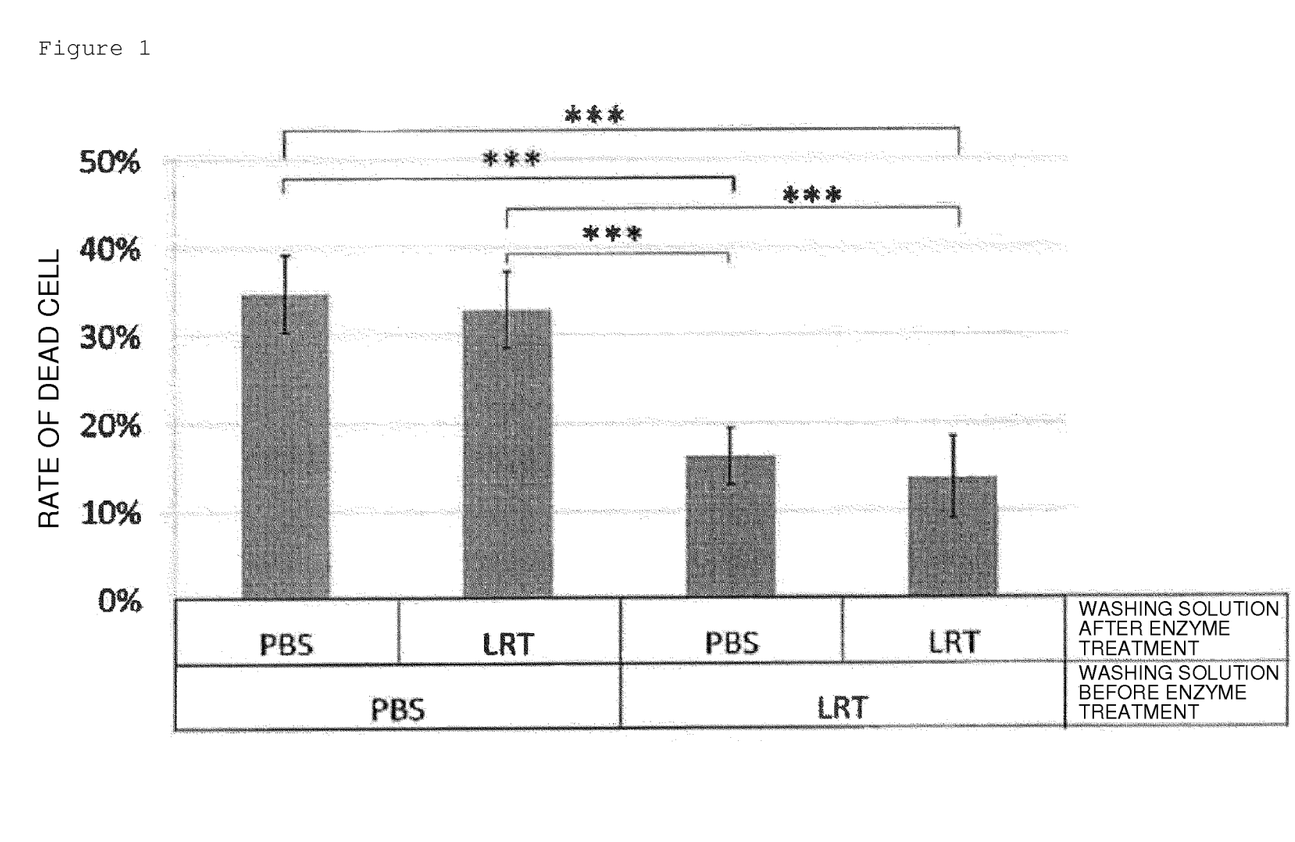
FIG. 1 is a graph showing the results of analyzing the effect of suppressing cell death when adherent cells were washed using LRT before trypsin treatment (in the figure, "washing solution before enzyme treatment; LRT, washing solution after enzyme treatment; PBS"). PBS was used as a control (in the figure, "washing solution before enzyme treatment; PBS, washing solution after enzyme treatment; PBS), and LRT was used after trypsin treatment as Comparative Example 1 (in the figure, "washing solution before enzyme treatment; PBS, washing solution after enzyme treatment; LRT"). The ordinate shows the rate of dead cells (mean±standard deviation, [n=8]). In the figure, "***" shows that a statistically significant difference exists by Tukey test between the 4 groups ($p<0.001$).

Whereas when the cells were washed using PBS before trypsin treatment, the rate of dead cells after trypsin treatment was 34.7% (FIG. 1, the 1st bar from the left), when the cells were washed using 3% LRT before trypsin treatment, the rate of dead cells after trypsin treatment was 16.3% (FIG. 1, the 2nd bar from the right); a statistically significant difference was observed between both of the rates ($p<0.001$). These results show that the washing of the cells using a physiological aqueous solution containing trehalose, such as LRT, before trypsin treatment decreases the rate of dead cells after trypsin treatment compared to that using a physiological aqueous solution not containing trehalose. As Comparative Example 1, when the cells were washed using PBS before trypsin treatment (the step of [1] in the "1-2 Method" of Example 1 above [washing treatment before enzyme treatment]) and the cells were washed using 3% LRT after trypsin treatment (the step of [4] in the "1-2 Method" of Example 1 above [washing treatment after enzyme treatment]), the rate of dead cells was 32.8% (FIG. 1, the 2nd bar from the left); this could confirm that the rate of dead cells was decreased, but not significantly, compared to when PBS as a control was used (FIG. 1, the 1st bar from the left, rate of dead cells: 34.7%); however, the effect was excellent to a larger extent when the cells were washed using 3% LRT before trypsin treatment ($p<0.001$, FIG. 1, comparison between the 2nd and 3rd bars from the left). When the cells were washed using 3% LRT before trypsin treatment and the cells were further washed using 3% LRT after trypsin treatment, the rate of dead cells after trypsin treatment was 13.8% (FIG. 1, the 1st bar from the right); this could confirm that the rate of dead cells was decreased, but not significantly, compared to when 3% LRT was used before trypsin treatment (FIG. 1, the 2nd bar from the right, rate of dead cells: 16.3%). These results show that the use of trehalose in cell washing after proteolytic enzyme treatment can further decrease the rate of dead cells by an additive or synergistic effect due to combination with the cell-washing solution of the present invention.

Example 2

2. Confirming that Cell Death-Suppressing Effect by Cell-Washing Solution of Present Invention is Due to Trehalose and Studying Time of Treatment with Cell-Washing Solution of Present Invention 2-1 Method In addition, to confirm that the effect of suppressing cell death by LRT was not due to LR but due to trehalose, an experiment when LR was used as a control for the washing solution before trypsin treatment was carried out. To simultaneously study cell-washing treatment time before trypsin treatment, the experiment was also carried out according to the procedures described in [1] to [5] below.

[1] The MSC medium was aspirated/removed from the 6-well dish to which hMSC-BM adhered, to which 2 mL/well of lactated Ringer's solution containing 3 (w/v) % trehalose (3% LRT) at 25° C. was then added, followed by incubation at 25° C. for 0.5, 1, 3, 5, 7, and 10 minutes (washing treatment before enzyme treatment). LR was used as a control, and PBS, which is commonly used for a washing solution, was used as also control.

[2] After aspirating/removing 3% LRT, 1 mL/well of a diluted trypsin-EDTA (from Lonza Group Ltd.) solution in which PBS maintained at 25° C. was mixed in equal amounts was added, followed by incubation at 25° C. for 20 minutes (enzyme treatment).

[3] The MSC medium at 25° C. was added by 1 mL to suspend the cells (enzyme reaction termination treatment), and then the cell suspension was transferred to a 15-mL conical centrifuge tube.

[4] Centrifugation was carried out at 600×g and 25° C. for 5 minutes, and the supernatant was aspirated/removed, followed by suspension in 100 µL of ice-cold PBS for each well (washing treatment after enzyme treatment).

[5] 10 µL of the cell suspension was taken and mixed with 10 µL of trypan blue, followed by measuring the number of cells using one cell counter under a microscope to evaluate the rate of dead cells.

2-2 Result

Figure 2:
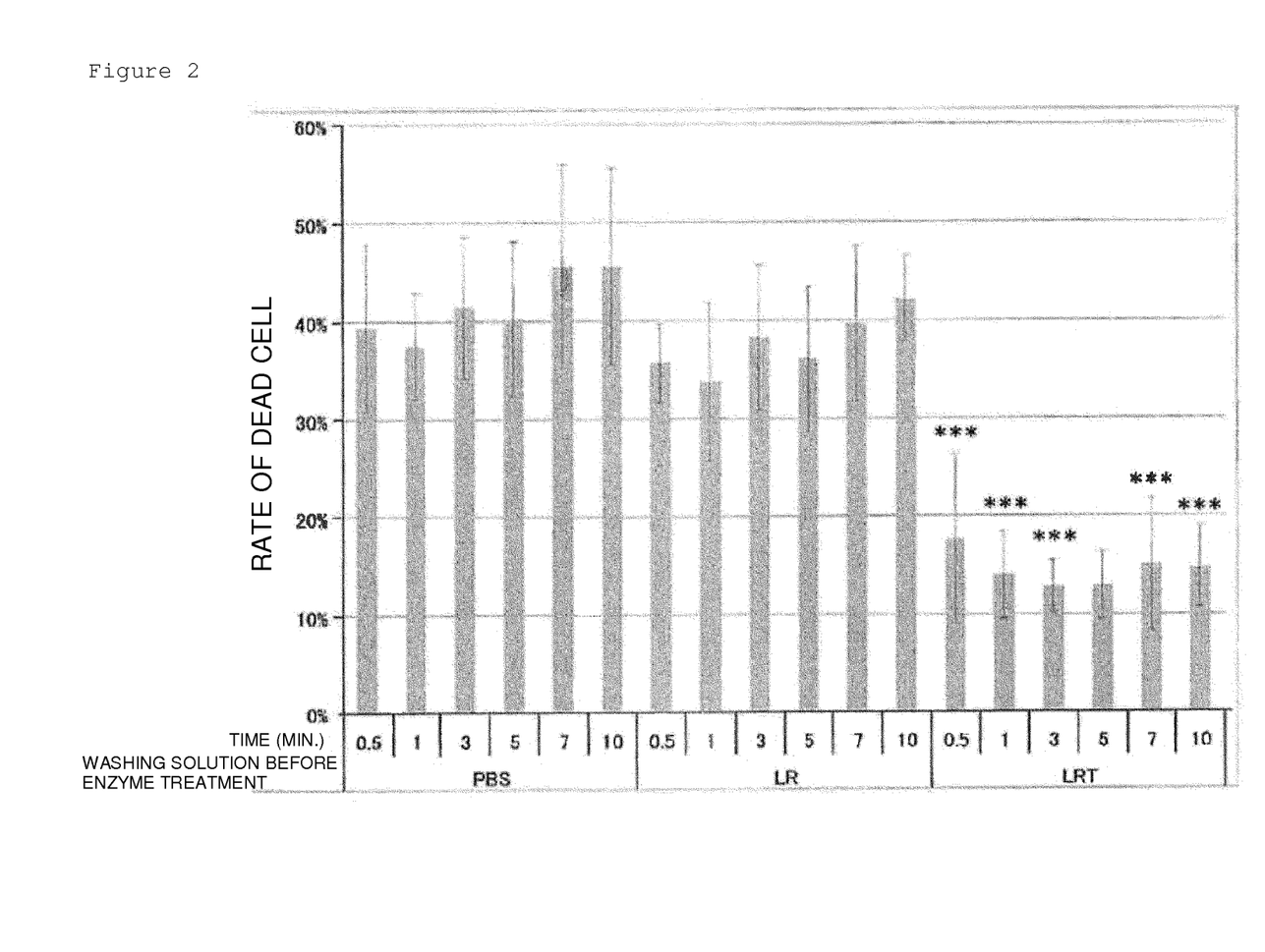
FIG. 2 is a graph showing the results of analyzing the effect of suppressing cell death when adherent cells were washed for 0.5 to 10 minutes using LRT before trypsin treatment. LR and PBS were used as controls. The ordinate shows the rate of dead cells (mean±standard deviation, [n=8]). In the figure, "***" shows that statistically significant differences against PBS and LR exist by Tukey test for each washing time ($p<0.001$).

The results are shown in FIG. 2. For example, for a washing treatment time before trypsin treatment of 10 minutes, whereas when the cells were washed using LR before trypsin treatment, the rate of dead cells after trypsin treatment was 42.1%, when the cells were washed using 3% LRT before trypsin treatment, the rate of dead cells after trypsin treatment was decreased to 14.8% (FIG. 2); the decrease was statistically significant ($p<0.001$). No statistical significant difference was observed between PBS and LR. These results show that the effect of suppressing cell death by the cell-washing solution of the present invention was not due to LR but due to trehalose. In addition, similarly for a time of cell-washing treatment with LRT before trypsin treatment of 0.5 to 7 minutes, the effect of suppressing cell death was observed to the same extent (FIG. 2). These results show that when treatment is performed at least in the range of 0.5 to 10 minutes using the cell-washing solution of the present invention before trypsin treatment, the effect of suppressing cell death is observed to the same extent.

Example 3

3. Study of Trehalose Concentration Applied to Cell-Washing Solution of Present Invention 3-1 Method Then, to study the trehalose concentration applied to the cell-washing solution of the present invention, an experiment was carried out according to the procedures described in [1] to [5] below.

[1] The MSC medium was aspirated/removed from the 6-well dish to which hMSC-BM adhered, to which 2 mL/well of lactated Ringer's solution containing each concentration (1, 3, 5, 7, 10, 12, or 15 [w/v]%) of trehalose at 25° C. was then added, followed by making heat retention at 25° C. for 1 minute (washing treatment before enzyme treatment). LR was used as a control.

[2] After aspirating/removing the washing solution before enzyme treatment of [1], 1 mL/well of trypsin-EDTA (from Lonza Group Ltd.) maintained at 25° C. was added, followed by incubation at 25° C. for 15 minutes (enzyme treatment).

[3] The MSC medium at 25° C. was added by 1 mL to suspend the cells (enzyme reaction termination treatment), and then the cell suspension was transferred to a 15-mL conical centrifuge tube.

[4] Centrifugation was carried out at 600×g and 25° C. for 5 minutes, and the supernatant was aspirated/removed, followed by suspension in 100 µL of ice-cold PBS for each well (washing treatment after enzyme treatment).

[5] 10 µL of the cell suspension was taken and mixed with 10 µL of trypan blue, followed by measuring the number of cells using one cell counter under a microscope to evaluate the rate of dead cells.

3-2 Result

Figure 3:
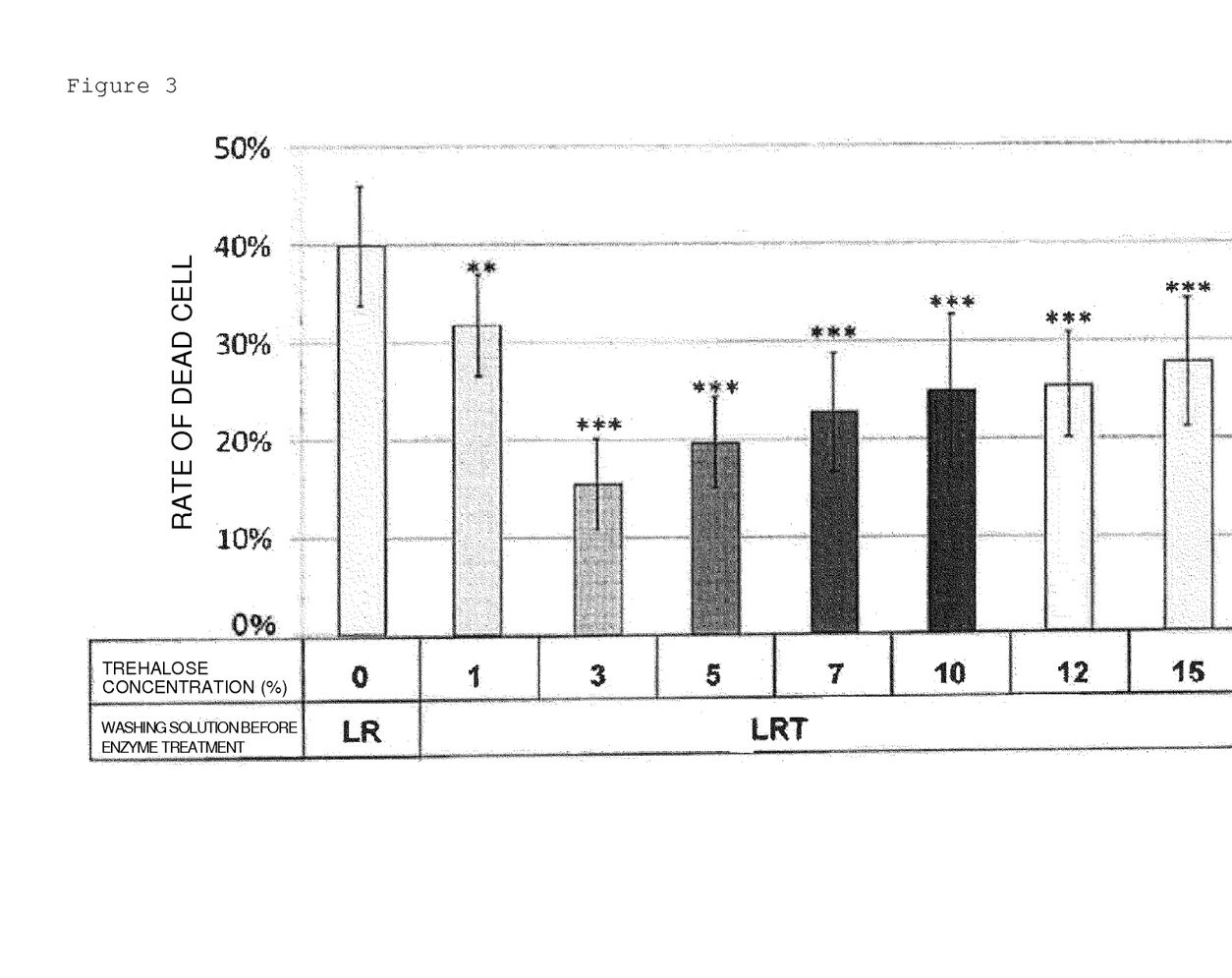
FIG. 3 is a graph showing the results of analyzing the effect of suppressing cell death when adherent cells were washed using LRT having each concentration (1, 3, 5, 7, 10, 12, or 15 [w/v]%) of trehalose before trypsin treatment. LR was used as a control. The ordinate shows the rate of dead cells (mean±standard deviation, [n=12]). In the figure, "" and "*" show that statistically significant differences against LR exist by Dunnett test ($p<0.005$ and $p<0.001$, respectively).

The results are shown in FIG. 3. When the cells before trypsin treatment was washed using LRT having a trehalose concentration of 1 to 15 (w/v) %, the rate of dead cells was decreased at each concentration thereof compared to when LR containing no trehalose was used (FIG. 3); the decrease was statistically significant. It was also revealed that when the cell-washing solution having a trehalose concentration of 3 (w/v) % was used, the effect of suppressing cell death was most outstanding. These results show that the effect of suppressing cell death is observed when the trehalose concentration applied to the cell-washing solution of the present invention is at least in the range of 1 to 15 (w/v) %, and also show that the particularly excellent effect of suppressing cell death is observed when the trehalose concentration is 1 to 7 (w/v) %, particularly 3 to 5 (w/v) %.

Example 4

4. Analysis of Effect of Suppressing Cell Death when Trehalose was Added in Trypsin Treatment or Trypsin Reaction Termination Treatment 4-1 Method Then, to analyze the effect of suppressing cell death when trehalose was added in trypsin treatment or trypsin reaction termination treatment, an experiment was carried out according to the procedures described in [1] to [5] below.

[1] The MSC medium was aspirated/removed from the 6-well dish to which hMSC-BM adhered, to which 2 mL/well of lactated Ringer's solution containing 3 (w/v) % trehalose at 25° C. was then added, followed by making heat retention at 25° C. for 1 minute (washing treatment before enzyme treatment). LR was used as a control.

[2] After aspirating/removing the washing solution before enzyme treatment of [1], 1 mL/well of a trehalose-containing trypsin solution maintained at 25° C., in which trehalose was added to a final concentration of 3 (w/v) % to trypsin-EDTA (from Lonza Group Ltd.) was added, followed by incubation at 25° C. for 15 minutes (enzyme treatment).

[3] A trehalose-containing MSC medium maintained at 25° C., in which trehalose was added to a final concentration of 3 (w/v) % to MSC medium was added by 1 mL to suspend the cells (enzyme reaction termination treatment), followed by transferring the cell suspension to a 15-mL conical centrifuge tube.

[4] Centrifugation was carried out at 600×g and 25° C. for 5 minutes, and the supernatant was aspirated/removed, followed by suspension in 100 μL of ice-cold PBS for each well (washing treatment after enzyme treatment).

[5] 10 μL of the cell suspension was taken and mixed with 10 μL of trypan blue, followed by measuring the number of cells using one cell counter under a microscope to evaluate the rate of dead cells.

4-2 Result

Figure 4:
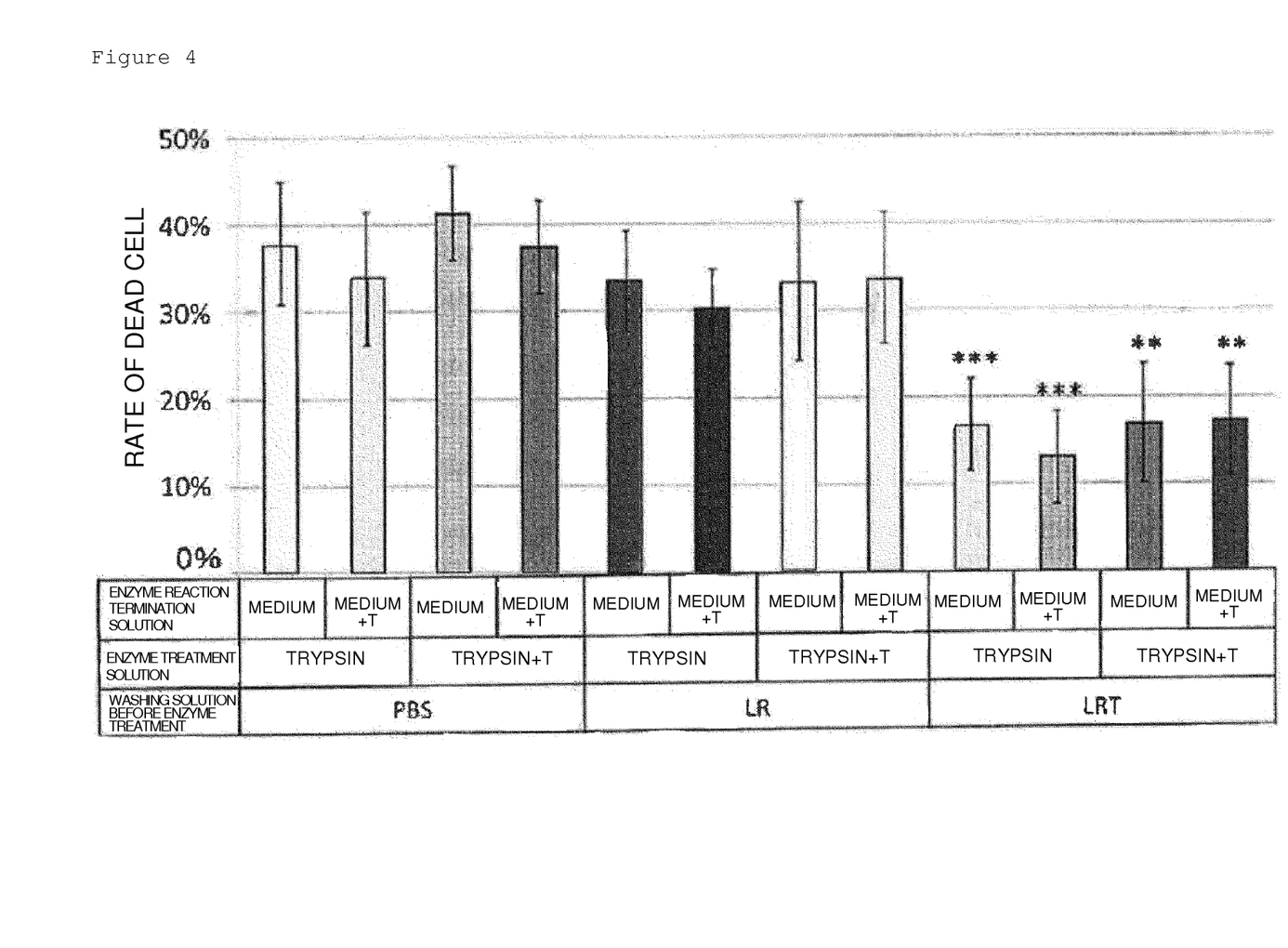
FIG. 4 is a graph showing the results of analyzing the effect of suppressing cell death when trehalose was added in trypsin treatment or in trypsin reaction termination treatment. In the figure, "trypsin+T" shows a trypsin solution containing trehalose, and in the figure, "medium+T" shows an FBS-containing human MSC medium containing trehalose. The ordinate shows the rate of dead cells (mean±standard deviation, [n=6]). In the figure, "*" shows that statistically significant differences against PBS and LR exist by Tukey test ($p<0.001$), and in the figure, "" shows that statistically significant differences against PBS and LR exist by Tukey test ($p<0.001$ and $p<0.005$, respectively).

The results are shown in FIG. 4. As Comparative Example 2, when the cells were washed using PBS before trypsin treatment and enzyme treatment was performed using the trehalose-containing trypsin solution (the step of [1] in "1-2 Method" of Example 1 above [washing treatment before enzyme treatment]), no change in the rate of dead cells was observed compared to when the trypsin solution containing no trehalose was used (comparison between "trypsin+T" and "trypsin" in FIG. 4). These results show that the addition of trehalose in proteolytic enzyme treatment cannot suppress the rate of dead cells. As Comparative Example 3, when the cells were washed using PBS before trypsin treatment and the trehalose-containing MSC medium ("medium+T" in FIG. 4) was used in trypsin reaction termination treatment (the step of [3] in "1-2 Method" of Example 1 above (enzyme reaction termination treatment)), the rate of dead cells was decreased compared to when the MSC medium containing no trehalose was used ("medium" in FIG. 4) (comparison between the 1st bar from the left in FIG. 4 [rate of dead cells: 37.9%] and the 2nd bar from the left in FIG. 4 [rate of dead cells: 33.9%]). These results show that when the cells are suspended using a protein-containing physiological aqueous solution, such as MSC medium, to which trehalose is added, in enzyme reaction termination treatment after proteolytic enzyme treatment, the rate of dead cells can be decreased, to a lesser extent, compared to when the cell-washing solution of the present invention is used. It could also be confirmed that when the cells were washed using 3% LRT before trypsin treatment and, further, a trehalose-containing MSC medium was used in trypsin reaction termination treatment, the rate of dead cells after trypsin treatment was 13.0% (FIG. 4, the 3rd bar from the right) and the rate of dead cells was decreased, but not significantly, compared to when 3% LRT was used before trypsin treatment (FIG. 4, the 4th bar from the right, rate of dead cells: 16.8%). These results show that the use of trehalose in proteolytic enzyme reaction termination treatment can further decrease the rate of dead cells by an additive or synergistic effect due to combination with the cell-washing solution of the present invention.

INDUSTRIAL APPLICABILITY

The present invention is useful in the field of medical transplantation in regenerative medicine or the like and the field of cancer treatment because it can decrease the percentage of dead cells in a cell suspension containing stem cells such as MSC to provide a good-quality cell suspension.

The invention claimed is:

1. A method of producing a cell suspension for transplantation, comprising:
    (a) removing medium from a culture vessel to which an adherent cell is adhered and washing the adherent cell with a cell-washing solution comprising a physiological aqueous solution with trehalose or its derivative or a salt thereof added thereto to obtain a washed adherent cell;
    (b) detaching the washed adherent cell from the culture vessel by proteolytic enzyme treatment;
    (c) suspending the adherent cell detached from the culture vessel in a protein-containing physiological aqueous solution to make a cell suspension; and
    (d) removing the solution in the cell suspension and washing the adherent cell with the physiological aqueous solution.

2. The method according to claim 1, wherein the adherent cell is a mesenchymal stem cell.

3. The method according to claim 1, wherein the cell-washing solution of (a) comprises trehalose or its derivative or a salt thereof in a concentration of 1 to 15 (w/v) %.

4. The method according to claim 1, wherein the proteolytic enzyme of (b) is trypsin.

5. The method according to claim 1, wherein the protein-containing physiological aqueous solution of
    (c) further comprises trehalose or its derivative or a salt thereof.

6. The method according to claim 1, wherein the protein-containing physiological aqueous solution of (c) is a serum-containing basal medium for animal cell culture.

7. The method according to claim 1, wherein the physiological aqueous solution of (d) further comprises trehalose or its derivative or a salt thereof.

* * * * *